(12) United States Patent
Kiermasz

(10) Patent No.: US 9,995,783 B2
(45) Date of Patent: Jun. 12, 2018

(54) MEASUREMENT APPARATUS AND METHOD

(71) Applicant: METRYX LIMITED, Bristol (GB)

(72) Inventor: Adrian Kiermasz, Bristol (GB)

(73) Assignee: METRYX LIMITED, Bristol (GB)

( * ) Notice: Subject to any disclaimer, the term of this patent is extended or adjusted under 35 U.S.C. 154(b) by 0 days. days.

(21) Appl. No.: 15/195,131

(22) Filed: Jun. 28, 2016

(65) Prior Publication Data

US 2016/0306004 A1 Oct. 20, 2016

Related U.S. Application Data

(63) Continuation of application No. 14/007,344, filed on Sep. 25, 2013, now Pat. No. 9,423,447.

(30) Foreign Application Priority Data

Apr. 7, 2011 (GB) .................................. 1105953.2

(51) Int. Cl.
*G01R 31/00* (2006.01)
*G01R 31/26* (2014.01)
(Continued)

(52) U.S. Cl.
CPC .......... *G01R 31/2601* (2013.01); *G01N 5/00* (2013.01); *G01N 5/02* (2013.01); *G01N 15/0893* (2013.01); *H01L 22/12* (2013.01); *C30B 1/00* (2013.01); *C30B 7/00* (2013.01); *C30B 23/00* (2013.01); *G01N 1/00* (2013.01); *G01N 2201/00* (2013.01); *G01N 2203/00* (2013.01); *H01J 49/26* (2013.01)

(58) Field of Classification Search
CPC .. G01N 1/00; G01N 2201/00; G01N 2203/00; C30B 23/00; C30B 1/00; C30B 7/00
See application file for complete search history.

(56) References Cited

U.S. PATENT DOCUMENTS 6,125,687 A * 10/2000 McClelland ............. G01N 5/00
422/80
2001/0013161 A1* 8/2001 Kitano ................ G03F 7/70991
29/25.01

(Continued)

OTHER PUBLICATIONS

GB Search Report Under Section 17, Application No. GB1105953.2, Dated: Aug. 25, 2011.

*Primary Examiner* — Jermele M Hollington
*Assistant Examiner* — Temilade Rhodes-Vivour
(74) *Attorney, Agent, or Firm* — Buchanan Ingersoll & Rooney PC

(57) ABSTRACT

A method and apparatus for extracting the contents of voids and/or pores present in a semiconductor device to obtain information indicative of the nature of the voids and/or pores, e.g. to assist with metrology measurements. The method includes heating the semiconductor wafer to expel the contents of the voids and/or pores, collecting the expelled material in a collector, and measuring a consequential change in mass of the semiconductor wafer and/or the collector, to extract information indicative of the nature of the voids. This information may include information relating to the distribution of the voids and/or pores, and/or the sizes of the voids and/or pores, and/or the chemical contents of the voids and/or pores. The collector may include a condenser having a temperature-controlled surface (e.g. in thermal communication with a refrigeration unit) for condensing the expelled material.

8 Claims, 7 Drawing Sheets

(51) Int. Cl.
  *G01N 5/02* (2006.01)
  *G01N 15/08* (2006.01)
  *H01L 21/66* (2006.01)
  *G01N 5/00* (2006.01)
  *C30B 7/00* (2006.01)
  *G01N 1/00* (2006.01)
  *C30B 1/00* (2006.01)
  *C30B 23/00* (2006.01)
  *H01J 49/26* (2006.01)

(56) References Cited

U.S. PATENT DOCUMENTS

| | | | |
|---|---|---|---|
| 2003/0052721 A1* | 3/2003 | Chaudhry | H01L 21/82285 327/242 |
| 2005/0063865 A1* | 3/2005 | Bonne | B82Y 15/00 422/68.1 |
| 2005/0199078 A1* | 9/2005 | Temmler | G01B 21/18 73/866 |
| 2005/0250297 A1* | 11/2005 | Shive | H01L 21/3221 438/471 |
| 2006/0175601 A1* | 8/2006 | Lieber | B82Y 10/00 257/19 |
| 2007/0119479 A1* | 5/2007 | Yoshihara | H01L 21/67253 134/18 |
| 2008/0213365 A1* | 9/2008 | Ediger | C23C 14/10 424/474 |
| 2008/0264443 A1* | 10/2008 | Shrinivasan | B08B 7/0021 134/2 |
| 2009/0229648 A1* | 9/2009 | Makansi | B82Y 10/00 136/201 |
| 2009/0261299 A1* | 10/2009 | Watanabe | C30B 25/20 252/500 |

* cited by examiner

MEASUREMENT APPARATUS AND METHOD

CROSS-REFERENCE TO RELATED APPLICATION

This application is a continuation of U.S. patent application Ser. No. 14/007,344, filed Sep. 25, 2013, which was a 371 Application of PCT/GB2012/050776, filed Apr. 5, 2012, both herein incorporated by reference.

TECHNICAL FIELD

This invention relates to semiconductor device metrology.

BACKGROUND TO THE INVENTION

Microelectronic devices are fabricated on semiconductor wafers using a variety of techniques, e.g. including deposition techniques (CVD, PECVD, PVD, etc) and removal techniques (e.g. chemical etching, CMP, etc). During the fabrication process, various layers of metal and/or dielectric material are formed as a structure on a semiconductor wafer base, for example on a silicon wafer base.

The surface on which a given layer of metal or dielectric material is formed may have a number of topographical features which need to be coated by that layer. These topographical features may be due to the underlying topography of the semiconductor wafer, or topographical features formed on a previous layer. Examples of topographical features that may need to be coated include trenches and vias.

When a layer is formed on a surface having topographical features such as a trench or a via, voids may be formed in the resulting structure. For example, when a layer of a material is deposited on a surface having a trench, the deposited material may build up on the elongate sides of the trench until material on opposing sides of the trench meet along a centre-line of the trench, forming a seam, i.e. a line along which the regions of material on opposing sides of the trench contact each other. Voids may be formed within the trench under this seam. A plurality of voids may be distributed along the seam. Voids may be more likely to occur where the walls of the trench are not uniformly flat, e.g. where there is a protruding lip along one or more upper edges of the trench.

FIG. 1 schematically shows a cross-section through a structure formed on a semiconductor wafer base. A layer of material 1, for example copper, has been deposited on a silicon wafer base 3. The deposited layer 1 covers a trench 5 on the surface 7 of the silicon wafer base 3. During the deposition process, material 1 has built up on the elongate sides 9 of the trench 5 until material on opposing sides 9 of the trench 5 has met along a seam 11. A void 13 has been formed in the trench beneath the seam 11.

FIG. 2 schematically shows a cross-section through a structure formed on a semiconductor wafer base. Features in common with the arrangement shown in FIG. 1 are given the same reference numbers and description thereof is not repeated. A via 15 is located within the trench 5. When the layer of material 1 was deposited on the surface 7 of the silicon wafer base 3, a void 17 was formed within the via 15.

Voids such as those shown in FIGS. 1 and 2 can be detrimental to semiconductor reliability. Such voids can give rise to electrical failures during operation of a semiconductor device. Where there is a void, there may be insufficient material to allow electrical conduction, thereby producing a short in the wiring of the semiconductor device. Also, voids might give rise to current going through a smaller conductive area, which may lead to heating and eventual failure of the semiconductor device. At present, it is not possible to tell how many voids there are in a structure formed on a silicon wafer base, or to determine information about any such voids, e.g. their size or distribution within the layer or structure.

Voids formed in the structure, such as those shown in FIGS. 1 and 2, may contain liquid or gas. The liquid or gas may be material which was present when the layer was deposited on the semiconductor wafer. For example, where a layer is deposited by plating, e.g. plating of copper, a liquid is applied to the surface to be coated. In the case of copper plating, this liquid may contain sulphuric acid. Thus, when a layer of copper is plated on a semiconductor wafer it is possible that voids containing liquids such as sulphuric acid may be present in the resulting structure.

In some circumstances, pores and/or voids are preferentially introduced into a coating layer on a semiconductor wafer. When fabricating a microelectronic device it is known to apply a coating layer of a material having a lower dielectric constant relative to the dielectric constant of silicon dioxide, for example a layer of SiOC (carbon doped silicon oxide). These materials are commonly referred to as low-K (or low-k) materials. The dielectric constant of silicon dioxide is 3.9. Air has a dielectric constant of approximately 1.00005. Thus, it is possible to reduce the dielectric constant of a porous coating layer relative to the dielectric constant of silicon dioxide by increasing the porosity of the coating layer, i.e. by reducing the average density of the material in the coating layer.

Known forms of porous dielectric material used when fabricating microelectronic devices include aerogels and xerogels. A xerogel is a solid formed from a gel by drying the gel with unhindered shrinkage. Xerogels can have porosity as high as 25% or greater. An aerogel is formed when solvent is removed from a wet gel under supercritical conditions, i.e. at a temperature and pressure above the critical point of the solvent. Due to the supercritical drying, aerogels retain the highly porous structure that the gel had in the wet stage, resulting in a structure with a very low density and high porosity.

The porosity of such layers may be further increased through the use of porogens. A porogen is a piece of material incorporated into the structure of the coating layer which can subsequently be removed, e.g. by thermal treatment, to leave behind a void in the coating layer. By artificially introducing voids into the coating layer in this manner, the porosity of the coating layer is increased and the dielectric constant of the material is reduced.

Scanning electron microscopy techniques, Rutherford back-scattering spectroscopy, small-angle neutron scattering (SANS) and ellipsometric porosimetry have been used to determine the mean pore size of porous dielectric materials. It is known to evaluate the pore content of a porous material based on the adsorption/condensation of an appropriate adsorptive in the pores. From the isotherm of adsorption, i.e. a plot of the amount of adsorbed/condensed adsorptive versus the relative pressure of the adsorptive at a constant temperature, it is possible to calculate an estimate of the porosity and the porous size distribution of the porous material. Such techniques require the porous material to be exposed to an adsorptive vapour while the porous material is in a vacuum.

With porous dielectric layers, it is possible that the voids may contain solid material lining the void, liquid material or gas, for example moisture or some remaining porogen material.

In some circumstances, an air gap is preferentially introduced into a semiconductor device, e.g. to provide a layer of air between a coating layer and the semiconductor wafer. Such air gaps may contain solid material, liquid material or gas, e.g. by-products of the process used to produce the air gap.

SUMMARY OF THE INVENTION

At its most general, the present invention proposes a method and apparatus for extracting the contents of voids and/or pores present in a semiconductor device to obtain information indicative of the nature of the voids and/or pores, e.g. to assist with metrology measurements. This information may include information relating to the distribution of the voids and/or pores, and/or the sizes of the voids and/or pores, and/or the chemical contents of the voids and/or pores. The extraction step involves heating the semiconductor device to expel the material contained in the pores and/or voids of the semiconductor device and collecting the expelled material with a collector.

According to one aspect of the invention, there may be provided a semiconductor wafer metrology method comprising: heating a semiconductor wafer to expel material contained in voids formed in or beneath a layer deposited on the semiconductor wafer; collecting the expelled material in a collector, and measuring a consequential change in mass of the semiconductor wafer and/or the collector, to extract information indicative of the nature of the voids.

The consequential change in mass of the semiconductor device may be due to the removal of the expelled material. The consequential change in mass of the collector may be due to the collection of the expelled material. Both changes in mass can be used as indicators of the amount of material that is expelled from the semiconductor wafer when it is heated. The mass of material that is expelled from the semiconductor device when it is heated is indicative of the nature of the voids in or beneath the deposited layer. For example, the mass of expelled material may be indicative of the total size (i.e. volume) of the voids present in the semiconductor wafer, as a greater mass may be expelled where there are more voids in the semiconductor wafer.

The changes in mass mentioned herein may be obtained by comparing a mass measurements taken before the heating step with one or more mass measurements taken during or after expulsion of the material in the voids.

The method may have one, or to the extent that they are compatible, any combination of the following optional features.

The semiconductor wafer may be heated by applying heat to a surface of the semiconductor wafer opposite to a surface on which the layer is deposited. Heating the semiconductor wafer on a surface opposite to the surface on which the layer is deposited may enable the collector to be located in close proximity to the layer without the collector being heated to the same temperature as the layer, i.e. a temperature gradient may exist between the layer deposited on the semiconductor wafer and the collector.

The semiconductor wafer may be heated by a heat source that is in thermal contact with the surface of the semiconductor wafer opposite to the surface on which the layer is deposited. For example, the semiconductor device may be heated by bringing it into contact with a hot surface, e.g. a heated plate.

The method may include the step of controllably adjusting the temperature of the semiconductor device, e.g. using an adjustable heat source, and measuring the change in mass of the semiconductor device due to the expelled material and/or the change in mass of the collector due to the collected material as a function of the temperature of the semiconductor device. Thus, a change in mass of the semiconductor device and/or a change in mass of the collector may be linked to the particular temperature, or range of temperatures, at which that change in mass occurs. The temperature at which material is expelled from the semiconductor device will be related to the type of the material, i.e. a higher or lower temperature may be required to expel liquid sulphuric acid from a void in the semiconductor device than is required to expel liquid water from a void in the semiconductor device. Therefore, by measuring the temperature or temperature range in which a material is expelled from the semiconductor device, it may be possible to identify the type of that material.

Measuring the change in mass of the semiconductor device and/or the change in mass of the collector as a function of the temperature of the semiconductor device may include measuring the mass of the semiconductor device and/or the mass of the collector a plurality of times as the temperature of the semiconductor device is gradually increased. Alternatively, the temperature of the semiconductor device may be increased in a series of step changes, i.e. sharp increases in temperature, and the change in mass of the semiconductor device and/or the change in mass of the collector may be measured between neighbouring step changes in temperature. For example, the temperature of the semiconductor device may be maintained at temperature T1 between times t1 and t2 and then temperature T2 between times t2 and t3. The change in mass of the semiconductor device and/or the change in mass of the collector may be measured between times t1 and t2 and again between times t2 and t3.

The expelled material may be gas or vapour. The collector may be a condenser for condensing (i.e. causing a phase change to a non-gaseous state) the gaseous or liquid vapour expelled material. The expelled material may therefore be retained in or on the condenser in non-gaseous (e.g. liquid or solid) form. The condenser may, for example, be a cooled surface, e.g. a condensing plate.

In the step of collecting the expelled material, the condenser may be positioned opposite to the surface of the semiconductor wafer on which the layer is deposited. As material is expelled from the semiconductor device it may contact the condenser and condense, leading to the collection of the majority or all of the expelled material in the condenser. When the condenser is positioned opposite to the surface of the semiconductor device, expelled material may be condensed opposite to the void from which it was expelled. Thus, the expelled material may be expelled from the semiconductor device perpendicular to the layer and may therefore contact the condenser opposite to the point on the layer from which it was expelled. Therefore, the locations of condensed expelled material on the condenser may reflect, or map, the locations of the voids in the semiconductor device, i.e. the locations of the condensed material may be representative of the locations of the voids. The locations of condensed material on the condenser may more accurately represent the locations of the voids when the condenser is closely spaced from the semiconductor device. For example, the condenser may be spaced from the semiconductor device by a separation of less that one millimeter. In some embodiments, the condenser may be in contact with the surface of the semiconductor device.

In the step of collecting the expelled material, a vacuum may be provided in a gap between the semiconductor device and the condenser, i.e. the semiconductor device and the condenser may be separated by a gap occupied by a gas at a low pressure. The vacuum may be an extremely high vacuum, i.e. a gas at a pressure of less than $10^{-10}$ Pa. Preferably, the vacuum is at a pressure of 0.1 Pa or less, e.g. between $10^{-9}$ Pa and 0.1 Pa. Providing a vacuum in the gap between the condenser and the semiconductor device may prevent the establishment of convection currents that may otherwise be caused by the temperature gradient between the hotter semiconductor device and the colder condenser. Convection currents in the gap between the semiconductor device and the condenser may move expelled material along the surface of the condenser before it is condensed on the condenser. If this occurs, the locations of condensed material on the condenser may no longer be representative of the locations of the voids in the semiconductor device. The pressure of the gas in the gap between the condenser and the semiconductor device may be related to the position of the condenser relative to the semiconductor device in order to facilitate representative condensation. For example, a suitable separation of the condenser from the semiconductor device may be determined from the expected or calculated velocity of the expelled material and/or the expected or calculated mean free path of the expelled material in the gas in the gap between the condenser and the semiconductor device. Alternatively, where the separation of the condenser from the semiconductor device is predetermined, a suitable pressure may be determined based on this separation.

The step of collecting the expelled material may include maintaining the temperature of the condenser at a particular temperature. The temperature at which the condenser is maintained must be sufficiently low to cause expelled material to be condensed when it contacts the condenser. The particular temperature at which the condenser is maintained may therefore be predetermined based on the type of material that is to be collected by the condenser. Alternatively, e.g. if the type of material to be collected by the condenser is unknown, the temperature of the condenser may be maintained at a particular temperature that is suitable for condensing a range of different materials.

The particular temperature at which the condenser is maintained may, for example, be the ambient temperature. Alternatively, the particular temperature may be sufficiently low to condense expelled material which is a gas at ambient temperature, for example a temperature of 73 K, the temperature of liquid nitrogen. Preferably, the temperature at which the condenser is maintained is between 73 K and 373 K. The temperature of the condenser need not be uniformly maintained at a particular temperature, i.e. the temperature of the condenser need not be uniform across the condenser or uniform with time, provided that at all times the maximum temperature of any part of the condenser is below the condensation temperature of expelled material.

The temperature of the condenser may be maintained at a particular temperature by cooling the condenser using a refrigeration unit. However, other methods of maintaining the condenser at a particular temperature may be used, for example using a liquefied gas to cool the condenser.

The method may further comprise the step of measuring the mass of the condenser as the temperature of the condenser is controllably increased from an initial temperature at which the expelled material was condensed. For example, the condenser may initially be cooled to a temperature sufficient to condense all of the material that is expelled from the semiconductor device. By measuring the mass of condensed material on the condenser as the temperature of the condenser is subsequently controllably increased, it may be possible to investigate the composition of the condensed material.

For example, the condensed material may comprise liquid A that evaporates at temperature T1 and liquid B that evaporates at temperature T2. As the temperature of the condenser is increased to a temperature greater than temperature T1, there will be a measurable change in the mass of condensate on the condenser as liquid A evaporates. When the temperature of the condenser reaches temperature T2, there will be another measurable change in the mass of condensate on the condenser as liquid B evaporates. By accurately determining the temperatures at which these changes in mass occur, it may be possible to identify the composition of the material, i.e. it may be possible to identify that the liquid comprises liquid A and liquid B.

Controllably increasing the temperature of the condenser may include smoothly and continuously increasing the temperature of the condenser. Alternatively, controllably increasing the temperature may include increasing the temperature of the condenser in a series of discrete step changes in temperature, i.e. a series of sharp increases in temperature.

In the step of collecting the expelled material, a surface of the condenser on which the expelled material is condensed may be partitioned into a plurality of separate condensing portions. Partitioning the condenser into separate condensing portions means that material that condenses on one condensing portion is prevented from combining with material that condenses on a neighbouring condensing portion. If the condenser were not partitioned in this manner, it is possible that when a large amount of expelled material is condensed on the condenser, neighbouring regions of condensate may combine. If this occurred, the regions of condensed material on the condenser would no longer be representative of the locations of the voids in the semiconductor device.

The size of the condensing portions fixes the effective resolution at which the locations of condensed material on the condenser map the locations of voids in the semiconductor device. The smaller the size of the condensing portions, i.e. the more condensing portions there are in a given condenser, the better the resolution. Preferably, the size of the condensing portions is of the order of, or smaller than, the size of the voids in the semiconductor device. Furthermore, it may be possible for the condensing portions to exhibit capillary action to move the collected material away from the surface of the collector.

The surface of the condenser may be partitioned into a uniform grid pattern of a plurality of separate condensing portions. A uniform grid pattern provides a uniform resolution across the condenser and therefore increases the uniformity of the mapping of the location of the voids in the semiconductor device.

The surface of the condenser may be partitioned into a plurality of separate condensing portions by one or more raised ribs on the surface. The raised ribs on the surface may prevent condensed material in neighbouring condensing portions from combining.

In the step of collecting the expelled material, the collector may be positioned so that the raised ribs on the surface of the condenser abut the layer of the semiconductor device.

Thus, when the raised ribs have a controlled and uniform height above the surface of the condenser, the condenser and semiconductor device may be accurately aligned in opposition to each other with a controlled spacing there-between. In addition, the raised ribs may effectively partition the gap between the condenser and the semiconductor device, thereby preventing convection currents from being set up in the gap. In this case, it may therefore be unnecessary to provide a vacuum in the gap between the condenser and the semiconductor device.

In the step of heating the semiconductor device to expel material contained in voids in the semiconductor device, the semiconductor device may be heated to a temperature sufficient to anneal material in the layer deposited on the semiconductor wafer. For example, where the layer is a layer of copper, the semiconductor device may be raised to a temperature sufficient to anneal the copper. When a metal such as copper is annealed, the previously amorphous structure of the metal changes to a grain structure. It is believed that during the formation of the grains, material previously trapped in voids within the semiconductor device may be expelled along the grain boundaries. Thus, heating the semiconductor device to a temperature sufficient to anneal material in the layer may ensure that all of the material contained in voids in the semiconductor device is expelled from the semiconductor device. It may be necessary to raise the temperature of the semiconductor device to a temperature above the annealing temperature to ensure that all of the material initially present in the voids is expelled from the semiconductor device.

However, it may not be necessary to heat the semiconductor device to the annealing temperature, as there may be other mechanisms that can lead to material being expelled from voids in the semiconductor device. For example, in the arrangement shown in FIG. 1, a seam 11 connects the void 13 to the surrounding atmosphere. Thus, if the temperature and pressure of the material in the void 13 is raised sufficiently, material in the void 13 may be expelled from the void 13 along the seam 11, without requiring the temperature of the device to be raised to a temperature sufficient to anneal the layer 1.

The method may further comprise the steps of locally heating a region of the condenser in order to evaporate any condensate in that region, and measuring the mass of the condensate evaporated from that region and/or the change in mass of the condenser due to the evaporated material. The change in mass of the condenser provides an indirect measurement of the mass of material evaporated from the condenser due to the local heating. Thus, it may be possible to determine whether there is any condensate present in a particular region of the condenser and if so how much condensate is present in that region. When the locations of condensate on the condenser are representative of the locations of voids in the semiconductor device, localised measurements of the amount of condensate in a region of the condenser may provide information indicative of the nature of the voids in a corresponding region of the semiconductor device. Where the semiconductor device and the condenser are closely spaced in opposition to each other, the corresponding region of the semiconductor device may be the region opposite to the region of the condenser that is being heated.

Following the step of collecting the expelled material in the condenser, the semiconductor wafer may be removed from the locality of the condenser, or the separation between the semiconductor wafer and the condenser may be significantly increased. Alternatively, the condenser may be removed from the locality of the semiconductor device. The condenser may then be locally heated by locally applying heat to a surface of the condenser opposite to a surface on which the expelled material is condensed. If the expelled material is condensed on a front surface, the condenser may be subsequently locally heated on a rear surface.

A number of possible methods are envisaged for locally applying heat to a region of the condenser. Heat may be applied using a laser. Alternatively, heat may be applied by infrared radiation. Alternatively, heat may be applied by a resistive heating element in thermal contact with a region of the condenser. Other known heating methods may also be used.

Different regions of the condenser may be sequentially locally heated, and the mass of condensate evaporated from each region and/or the change in mass of the condenser due to evaporated material from each region may be measured. This process may continue until the whole or a substantial part of the condenser has been locally heated. Thus, the locations at which condensate has formed on the condenser, and the amount of condensate formed at each of the locations, may be determined. Effectively, a map recording the location and mass of condensate formed on the condenser can be generated. When the locations at which condensate has formed on the condenser are representative of the locations of voids in the semiconductor device, the measured distribution of condensate across the condenser may effectively map the distribution of voids across the surface of the semiconductor device. The localised measurements of the mass of condensate in each region of the condenser may provide information indicative of the nature of the voids in corresponding regions of the semiconductor device. This information may include information relating to the number of voids in the corresponding regions of the semiconductor device, or information relating to the size of the voids in the corresponding regions. Thus, information relating to the distribution of the voids and the sizes of the voids may be simultaneously extracted.

Sequentially heating different regions of the condenser may, for example, involve moving the heat source relative to the condenser. For example, where heat is applied using a laser or an infrared source, the beam of radiation may be moved to alter the region of the condenser being heated. Where the heating is provided by a resistive heating element, the resistive heating element may be movable relative to the condenser. Alternatively, a plurality of fixed resistive heating elements, each of which is in thermal contact with a different region of the condenser, may be positioned on the rear surface of the condenser. Each of these elements may be independently activatable so that a single region of the condenser may be heated.

Where the condenser is partitioned into a plurality of condensing portions, the regions of the condenser that are locally heated may each correspond to different condensing portions. Thus, the temperature of each of the condensing portions may be independently increased by local heating, and the mass of condensate evaporated from each of the condensing portions, and/or the change in mass of the condenser due to the evaporation of material from each of the condensing portions, may be independently measured.

The method may include controllably adjusting the temperature of a region being locally heated and measuring the mass of the condensate evaporated from that region, and/or the change in mass of the condenser due to the evaporated material, as a function of the temperature of that region. The temperature at which condensate is evaporated from a region of the condenser is indicative of the type of the material in that region. Thus, by measuring the mass of the condensate evaporated from a region, and/or the change in mass of the condenser due to the evaporated material, it is possible to investigate the composition of the condensed material. The composition of the condensed material may be indicative of the contents of the voids in a corresponding region of the semiconductor device from which the condensed material was originally expelled.

Controllably adjusting the temperature of a region of the condenser may include smoothly and continuously increasing the temperature of that region. Alternatively, controllably increasing the temperature may include increasing the temperature of that region in a series of discrete step changes in temperature, i.e. a series of sharp increases in temperature.

The mass of material evaporated from a given region being locally heated may be measured using a mass spectrometer. Thus, the mass of evaporated material may be accurately measured.

Where the mass of evaporated material is measured using a mass spectrometer, the composition of the evaporated material may be analysed using the mass spectrometer. Thus, it may be possible to accurately determine both the mass and composition of the condensate present in a region of the condenser being locally heated.

According to another aspect of the invention, there may be provided semiconductor wafer metrology apparatus comprising: a heating portion for heating a semiconductor wafer to expel material contained in voids forming in or beneath a layer deposited on the semiconductor wafer, a collector for collecting the expelled material, and a mass measurement unit for measuring the consequential change in mass of the semiconductor wafer and/or the collector.

Features of the first aspect discussed above may be applicable to the second aspect.

The apparatus may have an alignment mechanism for aligning the semiconductor device and the collector (e.g. condenser) opposite each other.

The apparatus may further comprise a refrigeration unit for controlling, e.g. maintaining, the temperature of the condenser. The particular temperature at which the condenser is maintained may, for example, be the ambient temperature. Alternatively, the particular temperature may be sufficiently low to condense expelled material which is a gas at ambient temperature. The refrigeration unit may be adjustable so that the cooling of the condenser can be controllably adjusted, as explained above.

The apparatus may comprise a second heating portion for locally heating a region of the condenser in order to evaporate any condensate in that region. The mass of condensate evaporated from the region being locally heated may be indirectly measured by measuring the change in mass of the condenser using the mass measurement unit. Alternatively, the device may comprise a second mass measurement unit for directly measuring the mass of condensate evaporated from the region being locally heated. Thus, it may be possible to determine whether there is any condensate present in a particular region of the condenser and if so how much condensate is present in that region. When the locations of condensate on the condenser are representative of the locations of voids in the semiconductor device, localised measurements of the amount of condensate in a region of the condenser may provide information indicative of the nature of the voids in a corresponding region of the semiconductor device.

The second heating portion may comprise a second heat source for locally applying heat to a surface of the condenser opposite to a surface on which the expelled material is condensed. If the expelled material is condensed on a front surface, the condenser may be subsequently locally heated on a rear surface. The second heat source may be a laser or a source of infrared radiation. Alternatively, the second heat source may be a resistive heating element in thermal contact with a region of the condenser.

The second heating portion may be movable relative to the condenser to alter the region of the condenser being locally heated. Moving the heating portion relative to the condenser may involve translational movement of the heating portion relative to the condenser, or it may involve rotational movement of the heat source, e.g. where the heat source is a laser the laser may be rotated to alter the region of the condenser at which the laser beam is directed.

Alternatively, the second heating portion may comprise a plurality of fixed resistive heating elements, each of which is in thermal contact with a different region of the condenser. Each of these fixed resistive heating elements may be individually activatable so that a single region of the condenser may be heated. Where the condenser is partitioned into a plurality of condensing portions, these regions may correspond to different condensing portions. Thus, the temperature of each of the condensing portions may be independently increased by local heating, and the mass of condensate evaporated from each of the condensing portions may be independently measurable.

The second mass measurement unit may comprise a mass spectrometer. Thus, the mass of evaporated material may be measured to a high degree of accuracy. The mass spectrometer may also be used to analyse the composition of the evaporated material. Therefore, it may be possible to accurately determine both the mass and composition of the condensate present in the region of the condenser being locally heated.

BRIEF DESCRIPTION OF THE DRAWINGS

Embodiments of the invention will now be described by way of example with reference to the accompanying drawings, in which.

DETAILED DESCRIPTION; FURTHER OPTIONS AND PREFERENCES

Figure 1:
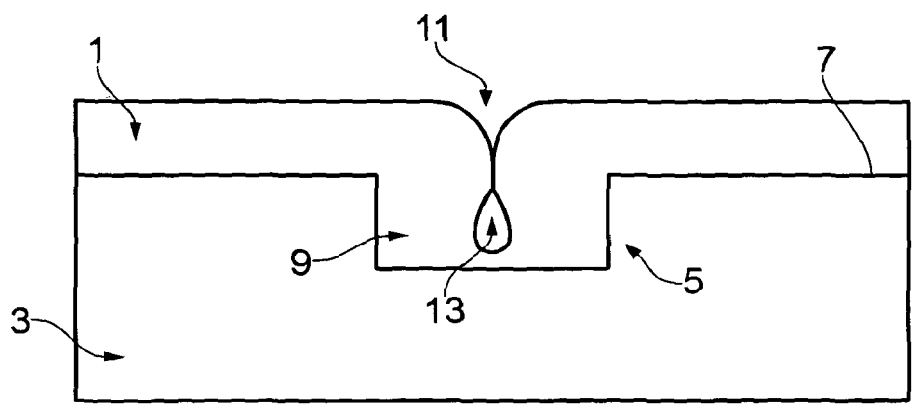
FIG. 1 schematically shows a cross-section through a structure formed on a semiconductor wafer base.
Figure 2:
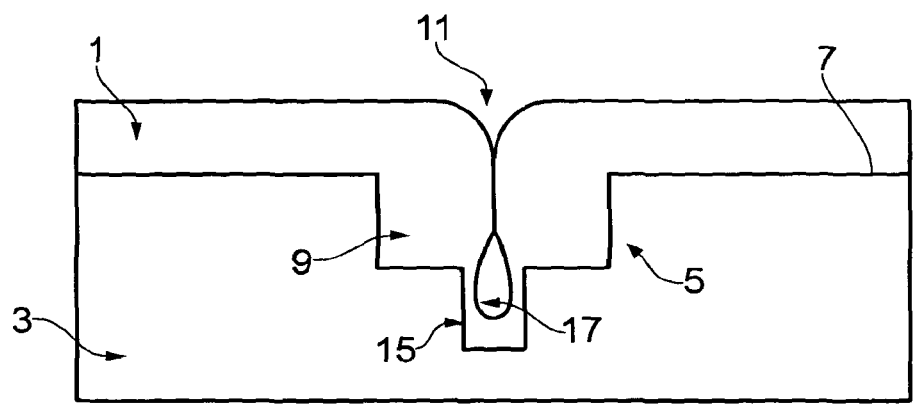
FIG. 2 schematically shows a cross-section through a structure formed on a semiconductor wafer base.

In one embodiment of the invention, a semiconductor wafer metrology method is provided in which the contents of voids in a semiconductor device which comprises a layer deposited on a semiconductor wafer are extracted. As illustrated in FIGS. 1 and 2, the voids in the semiconductor device may be voids 13, 17 formed when the layer is deposited on a surface having topographical features such as a trench 5 or a via 15. In these cases, the voids may contain material which was present when the layer was deposited on the surface, e.g. a liquid used when depositing a metal such as copper by plating, or a gas used when depositing a layer by a vapour deposition technique.

Figure 3:
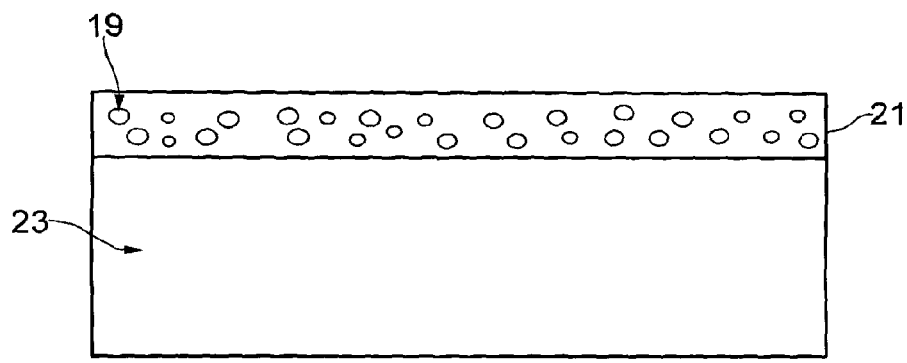
FIG. 3 schematically shows a cross-section through a porous layer formed on a semiconductor wafer base.

Alternatively, as illustrated in FIG. 3, the voids may be voids and/or pores 19 within a porous layer 21, e.g. a porous dielectric layer, deposited on a semiconductor wafer 23, e.g. a silicon wafer. The porous dielectric layer may be SiOC (carbon doped silicon oxide), or another porous dielectric material used in the fabrication of semiconductor devices. These voids and/or pores 19 may be voids and/or pores which naturally occur in aerogel or xerogel structures. Alternatively, they may be voids and/or pores which have been artificially introduced into the layer 21 using porogens. In these cases, the voids may contain moisture or remaining porogen material.

Alternatively, the void may be an air gap formed between a layer of material and the semiconductor wafer. Such an air gap may contain solid material, liquid material or gas, e.g. by-products of the process used to produce the air gap.

The layer may be directly deposited onto the semiconductor wafer, as in the arrangements illustrated in FIGS. 1 to 3. Alternatively, the layer may be deposited as part of a structure formed on the semiconductor wafer, i.e. the layer may be deposited on top of another layer rather than directly on the surface of the semiconductor wafer.

Figure 4:
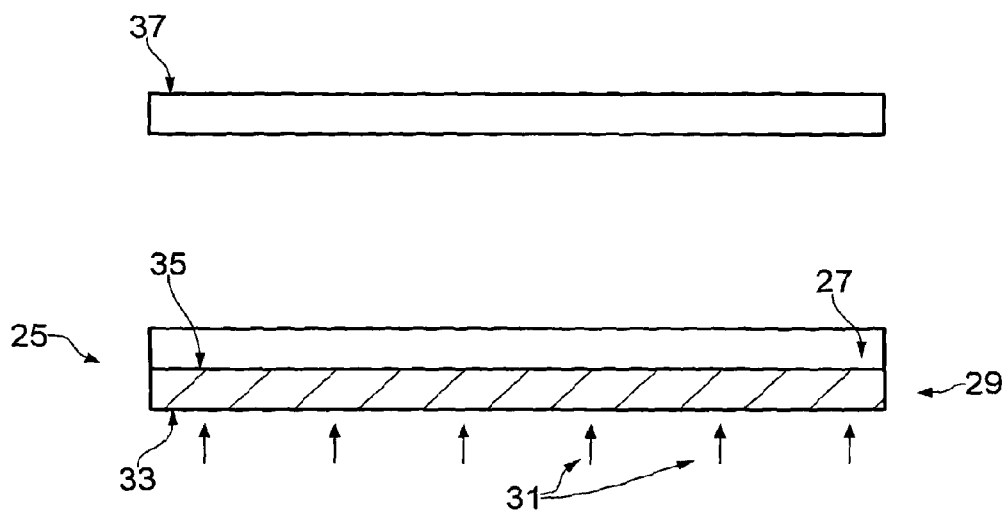
FIG. 4 schematically shows a semiconductor device being heated and a condenser positioned opposite to the semiconductor device.

In this embodiment, as illustrated in FIG. 4, a semiconductor device 25 which comprises a layer 27 formed on a semiconductor wafer 29 is heated by applying heat 31 to a surface 33 of the semiconductor wafer opposite to a surface 35 on which the layer 27 is deposited. In other embodiments, the semiconductor device may be heated differently. For example, the semiconductor device may be uniformly heated. A collector 37 is positioned opposite to the surface 35 of the semiconductor wafer 29 on which the layer 27 is deposited. In other embodiments, the collector may be differently positioned.

Figure 5:
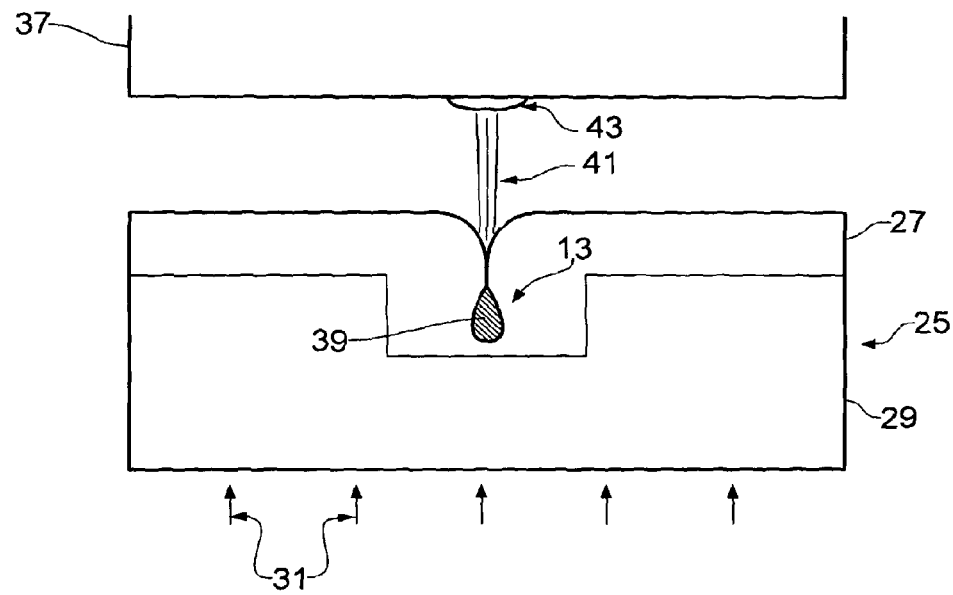
FIG. 5 schematically shows material being expelled from a semiconductor device and collected by a condenser.

As illustrated in FIG. 5, as the semiconductor device 25 is heated, material 39 contained in voids 13 of the semiconductor device 25 is expelled from the semiconductor device 25 as expelled material 41. For example, where the material 39 is initially in liquid form, it may be vaporised as the semiconductor device 25 is heated and may then be expelled from the semiconductor device 25 in vapour form. The expelled material 41 is collected by the collector 37. In this embodiment, the collector 37 is a condenser and the expelled material 41 is collected by condensing the expelled material 41 on the condenser to form condensate 43. In other embodiments, other types of collector for collecting expelled material may be used in place of a condenser.

As the semiconductor device 25 is heated, the change in mass of the semiconductor device 25 due to the expelled material 41 and/or the change in mass of the collector 37 due to the collected material 43 are measured to extract information indicative of the nature of the voids. For example, the information may be indicative of the number of voids present in the semiconductor device. Alternatively, the information may be indicative of the sizes of the voids in the semiconductor device.

In this embodiment, the method includes the step of controllably adjusting the temperature of the semiconductor device 25 and measuring the change in mass of the semiconductor device 25 due to the expelled material 41 and/or the change in mass of the collector 37 due to the collected material 43 as a function of the temperature of the semiconductor device 25. I.e. a change in mass of the semiconductor device 25 and/or a change in mass of the collector 37 may be linked to the particular temperature, or range of temperatures, at which that change in mass occurs. The temperature at which material 39 is expelled from the semiconductor device 25 will be related to the type of the material 39. Therefore, by measuring the temperature or temperature range in which a material 39 is expelled from the semiconductor device 25, it may be possible to identify the type of that material 39.

Figure 6:
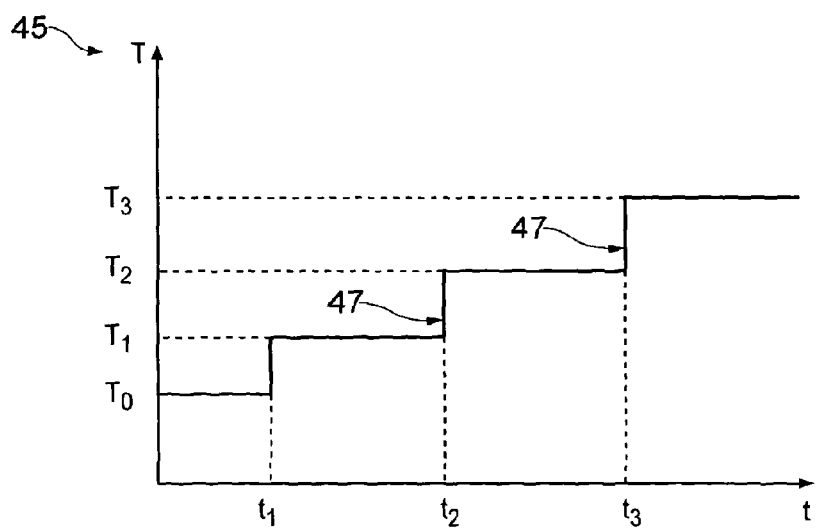
FIG. 6 is a schematic plot of an example temperature variation of a semiconductor device or a condenser with time.

As illustrated in FIG. 6, in an embodiment the temperature 45 of the semiconductor device 25 is controllably adjusted by increasing the temperature 45 in a series of step changes 47, i.e. sharp increases in temperature. In this embodiment, the temperature 45 of the semiconductor device 25 is maintained at temperature T1 between times t1 and t2. The temperature 45 of the semiconductor device 25 is increased in a step change to temperature T2 at time t2 and is then maintained at temperature T2 between times t2 and t3. The change in mass of the semiconductor device 25 and/or the change in mass of the collector 37 are separately measured between each pair of step changes 47 in temperature, i.e. between times t1 and t2 and again between times t2 and t3. The change in mass is therefore linked to the particular temperature range in which that change in mass occurs. In other embodiments, the temperature of the semiconductor device 25 may be smoothly and continuously increased with time, i.e. with no step changes 47 in the temperature.

In this embodiment, as illustrated in FIGS. 4 and 5, during the step of collecting the expelled material 41 the condenser 37 is closely spaced from the semiconductor device 25. As material is expelled from the semiconductor device 25 it will contact the condenser 37 and will be condensed, leading to the collection of the majority or all of the expelled material 41 in the condenser 37. When the condenser 37 is positioned opposite to the surface of the semiconductor device 25, expelled material 41 may be condensed opposite to the void 13 from which it was expelled. Therefore, the locations of condensed expelled material 43 on the condenser 37 may reflect, or map, the locations of the voids 13 in the semiconductor device 25, i.e. the locations of the condensed material 43 may be representative of the locations of the voids 13.

In this embodiment, to ensure that all of the expelled material 41 is collected by the condenser 37, the condenser 37 is cooled by a refrigeration unit and its temperature is maintained at a sufficiently low temperature to condense all of the expelled material 41.

Figure 7:
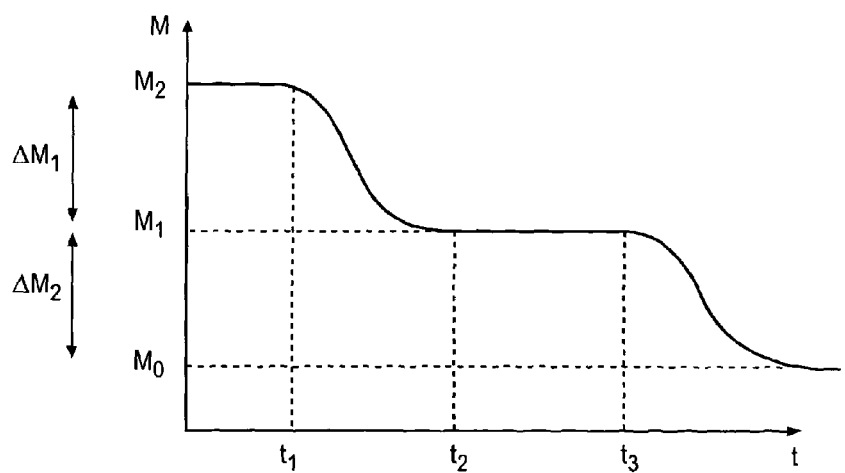
FIG. 7 is a schematic plot of an example variation in mass of a condenser as it is heated.

In some embodiments, the mass of the condenser 37 may be measured as the temperature of the condenser 37 is controllably increased from an initial temperature at which the expelled material 41 was condensed. The temperature of the condenser 37 may be controllably increased in a series of step changes 47, i.e. using a similar temperature profile to that illustrated in FIG. 6. Thus, it may be possible to investigate the composition of the expelled material 41. The mass of the condenser 37 may be continuously monitored as the temperature is increased, or alternatively the change in mass of the condenser 37 in a given time period may be measured. For example, where the expelled material 41 comprises liquid A that evaporates at a temperature between temperatures T0 and T1 and liquid B that evaporates at a temperature between temperatures T2 and T3 and the condenser is heated as shown in FIG. 6, the variation in the mass of the condenser 27 with time may be as shown in FIG. 7. When the temperature of the semiconductor device 25 is increased from T0 to T1 at time t1, liquid A evaporates and the mass of the condenser 37 decreases from M2 to M1. A change in mass of $\Delta M1$ is recorded between times t1 and t2. When the temperature of the semiconductor device 25 is increased from T2 to T3 at time t3, liquid B evaporates and the mass of the condenser decreases again from M1 to M0. A second change in mass of $\Delta M2$ is recorded between times t2 and t3. Thus, it is possible to identify the evaporation temperatures of liquids A and B within a range of temperatures and therefore it may be possible to identify what materials they are.

Figure 8:
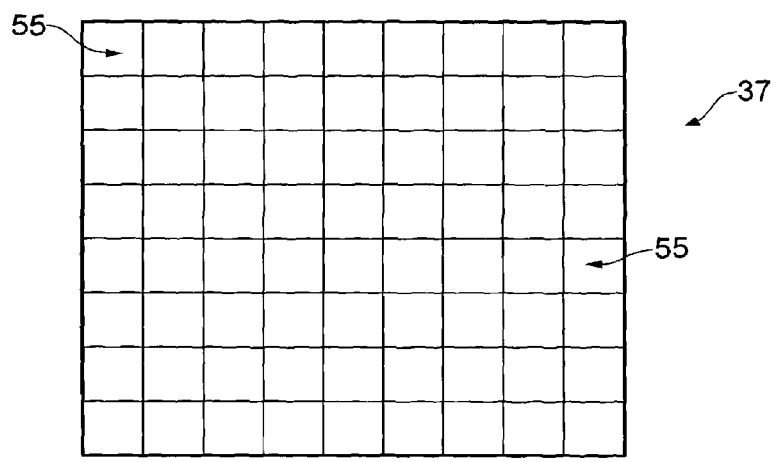
FIG. 8 schematically shows a plan view of a condenser that is partitioned into a plurality of condensing portions.

As illustrated in FIG. 8, in this embodiment a surface of the condenser 37 on which the expelled material 41 is condensed is partitioned into a uniform grid pattern of a plurality of separate condensing portions 55. In other embodiments, other arrangements of condensing portions 55 may be present other than a uniform grid pattern. In yet other embodiments, the surface of the condenser 37 may not be partitioned at all.

Figure 9:
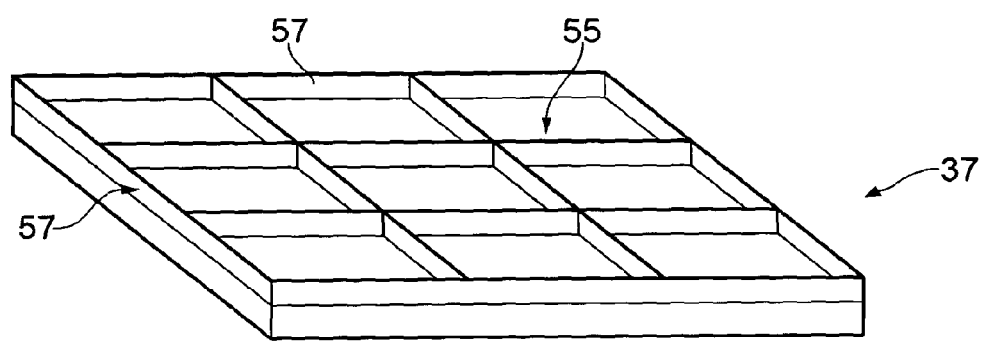
FIG. 9 schematically shows a view of a condenser that is partitioned into a plurality of condensing portions by a plurality of raised ribs.

Partitioning the condenser 37 into separate condensing portions 55 means that material that condenses on one condensing portion 55 is prevented from combining with material that condenses on a neighbouring condensing portion 55. If the condenser 37 were not partitioned in this manner, it is possible that when a large amount of expelled material 41 is condensed on the condenser 37, neighbouring regions of condensate 43 may combine. If this occurred, the regions of condensed material 43 on the condenser 37 would no longer be representative of the locations of the voids 13 in the semiconductor device 25. In this embodiment, the condenser 27 is partitioned into a plurality of separate condensing portions 55 by a plurality of raised ribs 57 on the surface of the condenser 37, as illustrated in FIG. 9. In other embodiments, other techniques may be used for partitioning the surface of the condenser 37.

Figure 10:
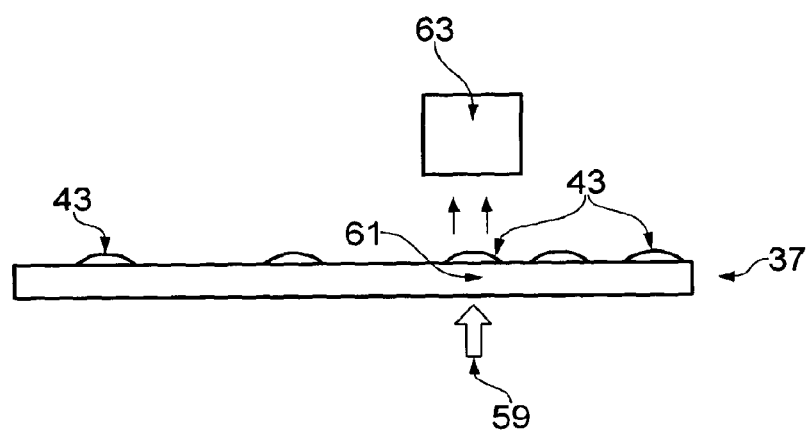
FIG. 10 schematically shows the step of evaporating condensed material from a condenser and measuring the mass of the evaporated material.

As illustrated in FIG. 10, the method according to this embodiment includes locally heating 59 a region 61 of the condenser 37 in order to evaporate any condensate 43 in that region. The mass of condensate 43 that is evaporated from the region 61 is measured directly in this embodiment by a second mass measurer 63. In other embodiments, the mass of condensate 43 that is evaporated from the region 61 may be measured indirectly by measuring the change in mass of the condenser 37. In this embodiment, different regions of the condenser 37 are sequentially heated, e.g. by moving a source of the local heating relative to the condenser 37, so that the mass of condensate 43 evaporated from each of a plurality of regions 61 which make up a whole or a substantial part of the condenser 37 is measured. Thus, the locations at which condensate 43 has formed on the condenser 37, and the amount of condensate 43 formed at each of the locations, may be determined. Effectively, a map recording the location and mass of condensate 43 formed on the condenser 37 can be generated. When the locations at which condensate 43 has formed on the condenser 37 are representative of the locations of voids 13, 17, 19 in the semiconductor device 25, the measured distribution of condensate 43 across the condenser 37 may effectively map the distribution of voids 13, 17, 19 across the surface of the semiconductor device 25. The localised measurements of the mass of condensate 43 in each region 61 of the condenser 37 may provide information indicative of the nature of the voids 13, 17, 19 in corresponding regions of the semiconductor device 25. This information may include information relating to the number of voids 13, 17, 19 in the corresponding regions of the semiconductor device 25, or information relating to the size of the voids 13, 17, 19 in the corresponding regions.

In this embodiment, the second mass measurer 63 for measuring the mass of condensate 43 locally evaporated from the condenser 37 is a mass spectrometer which is also used to analyse the composition of the evaporated condensate 43. In other embodiments, other mass measuring devices may be used to measure the mass of the evaporated condensate 43.

Figure 11:
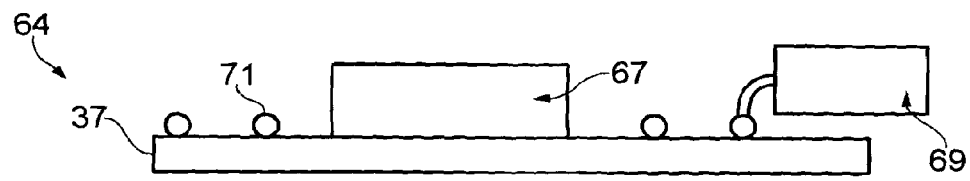
FIG. 11 schematically shows aspects of device according to the second aspect of the invention.
Figure 11:
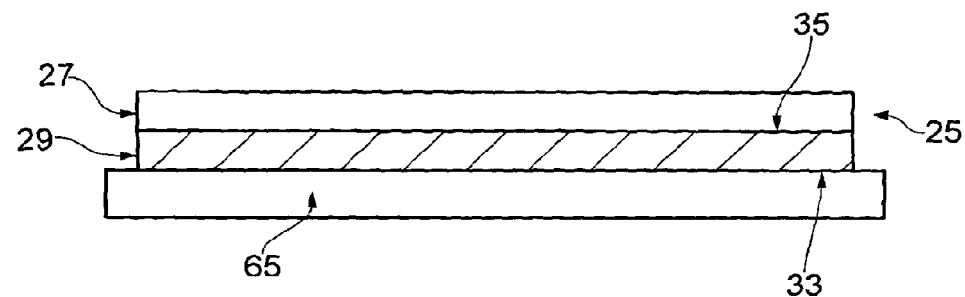

In another embodiment of the invention, as illustrated in FIG. 11, a device 64 is provided for extracting the contents of voids 13, 17, 19 in a semiconductor device 25 comprising a layer 27 deposited on a semiconductor wafer 29. The device 64 has a heating portion 65 for heating the semiconductor device 25 to expel material 39 contained in voids 13, 17, 19 of the semiconductor device 25. In this embodiment, the heating portion 65 is a heat source which is brought into thermal contact with a surface 33 of the semiconductor wafer 29 opposite to a surface 35 on which the layer 27 is deposited. For example, the heating portion may be a heated surface. In other embodiments, the heating portion 65 may not be in thermal contact with the semiconductor device 25, i.e. heat may be transferred to the semiconductor device 25 by e.g. radiative heating instead. Also, in other embodiments the semiconductor device 25 may be heated on a different surface or may be heated uniformly. The device 64 further has a collector 37 for collecting material expelled from voids 13, 17, 19 in the semiconductor device. In this embodiment, the collector 37 is a condenser and the expelled material 41 is collected by condensing the expelled material 41 on the condenser to form condensate 43. In other embodiments, other types of collector for collecting expelled material may be used in place of a condenser.

Figure 12:
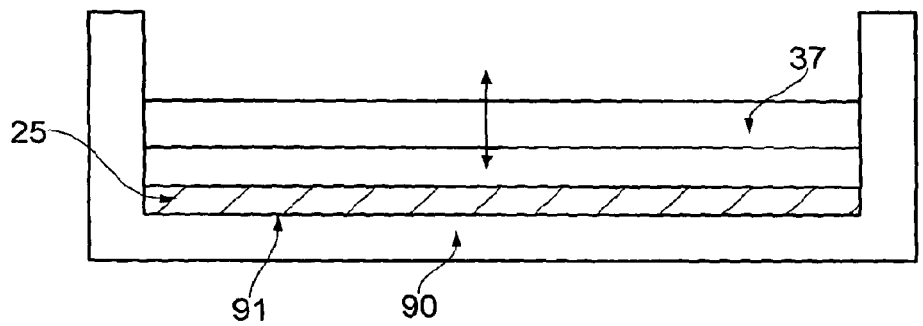
FIG. 12 schematically shows aspects of a device according to the second aspect of the invention.
Figure 13:
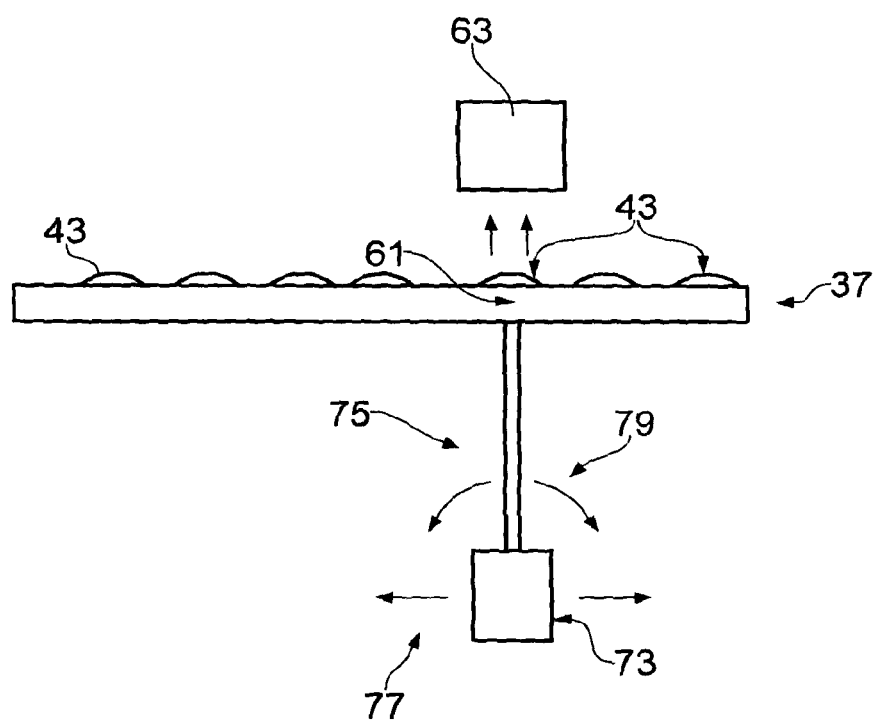
FIG. 13 schematically shows aspects of a device according to the second aspect of the invention.

As shown in FIG. 12, in this embodiment the semiconductor device 25 and the condenser 37 are arranged opposite each other using a mount 90. The semiconductor device 25 is positioned adjacent to a base 91 of the mount 90. The condenser 37 is slidably mounted in the mount 90 so that the separation of the condenser 37 and the semiconductor device 25 can be controllably varied. The semiconductor device 25 may have a notch, e.g. at an edge thereof, to indicate the crystal orientation of the semiconductor device 25. The mount 90 may have a corresponding protrusion so that the semiconductor device 25 can be positioned in the mount 90 with the protrusion received in the notch of the semiconductor device 25. For example, the protrusion may be a raised ridge. This ridge may extend perpendicular to the base 91 of the mount 90 and the condenser 37 may be slidable along this ridge to controllably vary the separation between the semiconductor device 25 and the condenser 37. In other embodiments, other known alignment devices may be used to align the semiconductor device 25 and condenser 37 in opposition to each other.

In this embodiment, the heating portion 65 is adjustable so that the temperature of the semiconductor device 25 can be controllably adjusted.

The device 64 includes a mass measurer 67 for measuring the change in mass of the condenser 37 due to the condensed material 43 to extract information indicative of the nature of the voids 13, 17, 19. For example, the information may be indicative of the number of voids 13, 17, 19 present in the semiconductor device 25. Alternatively, the information may be indicative of the sizes of the voids 13, 17, 19 in the semiconductor device 25. In other embodiments, the mass measurer 67 may be arranged to measure the change in mass of the semiconductor device 25 due to the expelled material 41 at the same time as, or instead of, measuring the change in mass of the condenser 37 due to the condensed material 43.

In this embodiment, the device 64 has a refrigeration unit 69 for controlling the temperature of the condenser 37. In this embodiment, the refrigeration unit provides cooled refrigerant to pipes 71 located adjacent to a rear surface of the condenser 37. In other embodiments, the pipes may be internal to the condenser 37. In yet further embodiments, other techniques for cooling the condenser 37, e.g. bringing a cooled liquid or gas into direct contact with the condenser 37 may instead be use to control the temperature of the condenser 37. In this embodiment the refrigeration unit 69 is adjustable so that the temperature of the condenser 37 can be varied. This can be achieved by adjusting the temperature or amount of the refrigerant in the pipes 71.

As illustrated in FIGS. 8 and 9, in some embodiments of the device a surface of the condenser 37 on which the expelled material 41 is condensed is partitioned into a uniform grid pattern of a plurality of condensing portion 55 by a plurality of raised ribs 57 on the surface of the condenser 37. In other embodiments, other techniques of partitioning the surface of the condenser 37 may be used, or the surface of the condenser 37 may not be partitioned at all.

In this embodiment, the device 64 has a second heating portion 73 for locally heating a region 61 of the condenser 37 in order to evaporate any condensate 43 in that region of the condenser 37. In this embodiment the second heating portion 73 is a laser for directing a laser beam 75 onto a surface of the condenser 37 opposite to a surface on which the expelled material 43 is condensed in order to locally heat a region 61 of the condenser 37. In other embodiments, other types of known heating device may be used in place of a laser.

In this embodiment the device 64 has a mass measurer for measuring the mass of any condensate 43 evaporated from the region 61 of the condenser 37. In other embodiments, the mass of condensate 43 evaporated from the condenser 37 may be indirectly measured by measuring the change in mass of the condenser 37 due to the evaporated material.

In this embodiment the laser 73 is movable relative to the condenser 37, either by translational movement of the laser 77 or rotational movement of the laser to alter the angle of the laser beam 75, to vary the region 61 of the condenser 37 being locally heated. Thus, the locations at which condensate 43 has formed on the condenser 37, and the amount of condensate 43 formed at each of the locations, may be determined. Effectively, a map recording the location and mass of condensate 43 formed on the condenser 37 can be generated. When the locations at which condensate 43 has formed on the condenser 37 are representative of the locations of voids 13, 17, 19 in the semiconductor device 25, the measured distribution of condensate 43 across the condenser 37 may effectively map the distribution of voids 13, 17, 19 across the surface of the semiconductor device 25. The localised measurements of the mass of condensate 43 in each region 61 of the condenser 37 may provide information indicative of the nature of the voids 13, 17, 19 in corresponding regions of the semiconductor device 25.

In this embodiment, the laser is adjustable, i.e. the power of the laser can be adjusted, so that the temperature of the region 61 of the condenser 37 being locally heated can be controllably adjusted.

The invention claimed is:

1. A semiconductor wafer metrology method comprising:
   heating a semiconductor wafer to expel material contained in enclosed voids formed in or beneath a layer deposited on the semiconductor wafer;
   collecting the expelled material in a collector; and
   measuring a consequential change in mass of the semiconductor wafer and/or the collector, to extract information indicative of the nature of the enclosed voids wherein the collector is a condenser having a temperature-controlled surface for condensing the expelled material.

2. A method according to claim 1, wherein heating the semiconductor wafer comprises applying heat to a surface of the semiconductor wafer opposite to a surface on which the layer is deposited.

3. A method according to claim 1 including positioning the temperature-controlled surface opposite to the surface of the semiconductor wafer on which the layer is deposited in order to collect the expelled material.

4. A method according to claim 1, wherein the temperature-controlled surface of the condenser is partitioned into a plurality of condensing portions.

5. A semiconductor wafer metrology method comprising:
   heating a semiconductor wafer to expel material contained in enclosed voids formed in or beneath a layer deposited on the semiconductor wafer;
   collecting the expelled material in a collector; and
   measuring a consequential change in mass of the semiconductor wafer and/or the collector, to extract information indicative of the nature of the enclosed voids;
   wherein heating the semiconductor wafer comprises gradually increasing the temperature of the semiconductor wafer, and wherein measuring the consequential change in mass of the semiconductor wafer and/or the collector comprises performing a plurality of mass measurement during the increase in temperature to obtain the consequential change in mass of the semiconductor wafer and/or the collector as a function of the temperature of the semiconductor wafer.

6. A semiconductor wafer metrology method comprising:
   heating a semiconductor wafer to expel material contained in enclosed voids formed in or beneath a layer deposited on the semiconductor wafer;
   collecting the expelled material in a collector;
   measuring a consequential change in mass of the semiconductor wafer and/or the collector, to extract information indicative of the nature of the enclosed voids; and
   after collecting the expelled material in the collector, applying localized heating to each of a plurality of regions of the collector to expel the collected material in each region, and measuring a consequential change in mass of the collector to extract information indicative of the nature of the collected material.

7. A semiconductor wafer metrology method comprising:
heating a semiconductor wafer to expel material contained in enclosed voids formed in or beneath a layer deposited on the semiconductor wafer;
collecting the expelled material in a collector; and
measuring a consequential change in mass of the semiconductor wafer and/or the collector, to extract information indicative of the nature of the enclosed voids; and
after collecting the expelled material in the collector, applying localized heating to each of a plurality of regions of the collector to expel the collected material in each region, and analyzing the expelled collected material.

8. A method according to claim 7, wherein analyzing the expelled collected material includes measuring the expelled collected material using a mass spectrometer.

* * * * *